US005800824A

United States Patent [19]

Pfrommer et al.

[11] Patent Number: 5,800,824

[45] Date of Patent: Sep. 1, 1998

[54] USE OF METAL OXIDE-DOPED ZINC OXIDES FOR COSMETIC PURPOSES

[75] Inventors: Ellen Pfrommer, Hassloch; Norbert Mronga, Dossenheim; Oliver Seeger, Mannheim, all of Germany

[73] Assignee: BASF Aktiengesellschaft, Ludwigshafen, Germany

[21] Appl. No.: 721,543

[22] Filed: Sep. 26, 1996

[51] Int. Cl.$^6$ .................................................... A61K 7/00

[52] U.S. Cl. ............................... 424/401; 424/59; 424/63

[58] Field of Search ................................ 424/59, 63, 401

[56] References Cited

U.S. PATENT DOCUMENTS

| | | | |
|---|---|---|---|
| 2,028,980 | 1/1936 | Kerinth et al. | 134/78 |
| 5,198,025 | 3/1993 | Dausch | 106/429 |
| 5,441,726 | 8/1995 | Mitchnick | 424/59 |

FOREIGN PATENT DOCUMENTS

| | | |
|---|---|---|
| 2059752 | 3/1993 | Canada . |

*Primary Examiner*—Thurman K. Page
*Assistant Examiner*—D. Faulkner
*Attorney, Agent, or Firm*—Keil & Weinkauf

[57] ABSTRACT

Metal oxide-doped colored zinc oxides are useful as colorants and UV absorbers in cosmetics.

6 Claims, No Drawings

USE OF METAL OXIDE-DOPED ZINC OXIDES FOR COSMETIC PURPOSES

The present invention relates to the use of metal oxide-doped colored zinc oxides for cosmetic purposes.

The colorants used in cosmetics, specifically decorative cosmetics, are frequently pigments. Pigments have high hiding power and good light stability compared with dyes. Important factors to be taken into account when choosing a pigment include not only the color properties, e.g. hue and brilliance, but also the toxicology. Generally, inorganic pigments are considered toxicologically safer than organic pigments. This is also reflected in the corresponding statutory provisions in the U.S.: the FDA has approved inorganic pigments as "exempt from certification", while organic pigments are "subject to certification" and therefore have to be tested and approved by the FDA on a batch-by-batch basis. In addition, in the U.S., many inorganic pigments are approved for the eye region, but only a few organic colorants.

In terms of color, however, organic pigments are frequently preferred, since they are more brilliant than existing inorganic pigments and thereby also make it possible to achieve a wider spectrum of hues. In the yellow-to-red region, brilliant hues have hitherto only been achievable with organic pigments. Iron oxides can be used among inorganic pigments, but they are distinctly duller in hue.

It is an object of the present invention to provide inorganic pigments which combine the advantageous properties of inorganic pigments (good fastness properties, good toxicology) with high color brilliance.

We have found that this object is achieved by the use of metal oxide-doped colored zinc oxides for cosmetic purposes, wherein the doped colored zinc oxides act as color pigments and/or UV absorbers.

Such doped zinc oxides are known for example from U.S. Pat. No. 2,028,980 or EP 482 444.

EP 482 444 describes a particularly suitable process for preparing doped zinc oxides which leads to particularly brilliant color pigments and which is characterized in that the oxides, carbonates, hydroxides and/or hydroxycarbonates of zinc are reacted with formic acid and/or oxalic acid in the presence of water and of oxides, carbonates, hydroxides, hydroxycarbonates, oxalates or formates of the doping metals to form the corresponding formates and/or oxalates, made into a paste, dried, ground and calcined at from 700° to 1100° C. in an inert gas atmosphere.

The zinc oxides prepared by the above-described processes are particularly highly suitable for the use according to this invention.

Suitable doping metals include in particular Ca, Fe, Mg and Mn in the form of the divalent metal oxides.

Very particular preference is given to Mn, which yields yellow to deep red color pigments, depending on the amount of the dopant used.

Similarly, mixtures of doping metals, e.g. Mn and Mg, are highly suitable for preparing the doped zinc oxides.

As to the preparation of the colored zinc oxides doped with metal ions, especially through the use of metal oxides, EP 482 444 and the references cited therein are expressly incorporated herein by reference.

The preparation of the doped zinc oxides is preferably effected by processing the oxides, carbonates, hydroxides and/or hydroxycarbonates of zinc in the presence of water and of oxides, carbonates, hydroxides, hydroxycarbonates, oxalates or formates of the doping metals into a paste using formic acid and/or oxalic acid in an amount which is at least sufficient for converting the aforementioned oxides, carbonates, hydroxides and/or hydroxycarbonates into formates or oxalates, drying the paste, grinding the dried paste, and calcining the ground dried paste at from 700° to 1100° C. in an inert gas atmosphere.

Possible metal oxides with which the zinc oxide can be doped are in particular the divalent oxides of Ca, Fe, Mn and Mg.

The process of preparation can be carried out by reacting the oxide, hydroxide, carbonate and/or hydroxycarbonate of divalent zinc and also the corresponding compounds of the divalent doping metals in the presence of water with formic acid and/or oxalic acid to form the corresponding formates and/or oxalates. The amount of water present is determined in such a way that the mixture has a pasty consistency. In general, this is the case with water contents of from 20 to 45% by weight, based on the other materials used. The reaction can be carried out at from 10° to 90° C. The acids are used at least in such amounts as are stoichiometrically necessary for converting the metal compounds used into the corresponding oxalates or formates. An excess of acid beyond the stoichiometrically required amount is not deleterious, but should advantageously not exceed 10%.

In a further version of the process of preparation, it is also possible to proceed stepwise by reacting the oxides, carbonates, hydroxides and/or hydroxycarbonates of the divalent doping metals with formic acid and/or oxalic acid in the presence of water and then introducing the zinc compounds into the resulting solution and reacting the mixture.

No filtration or washing of the product obtained in the first stage is necessary, since the amounts of water used are small and the reaction, in addition to the metal formates or oxalates, gives rise only to compounds which in the course of the subsequent drying or calcination will in any event be expelled from the reaction mixture.

The drying is customarily carried out at from 50° to 100° C. Following the drying, the product is ground and finally calcined at from 700° to 1100° C. in an inert gas atmosphere, such as a nitrogen or carbon dioxide stream. There is no need to add a reducing agent, since the formates or oxalates themselves have a reducing action and consequently there is no occurrence of an undesirable oxidation of the divalent doping metal oxides.

The pigments thus prepared are suitable for coloring decorative cosmetics, especially eye cosmetics such as eyeshadows, eyeliners, mascara, but also lipsticks, make-up and nail varnishes.

As well as colorant, zinc oxide is also used as UV absorber. Hitherto the conventional, white zinc oxide has been used for this purpose. The doped zinc oxide, then, makes it possible to prepare an inorganic pigment which can be used not only as a bright colorant but also as UV absorber.

The present invention also provides cosmetics comprising metal ion-doped colored zinc oxides.

The Examples which follow illustrate the invention.

EXAMPLE 1

Preparation of a lipstick with Mg- and Mn-doped zinc oxide (Sico-pal). The below-recited recipe was followed to prepare a lipstick base into which the tabulated amount and type of color pigment was incorporated. Four lipsticks were obtained (A–D).

3.0% of Permulgin 3430
4.0% of Permulgin 3450
3.0% of Permulgin 2550
3.5% of Permulgin 3220

3.5% of Permulgin 4200
1.5% of Cutina CP
6.0% of petrolatum
4.0% of Lanfrax
2.0% of lanolin
11.0% of Softisan 100
47.0% of ricinus oil The following doped zinc oxides were used as color pigments:

P1: Sicopal Yellow FK 4165 (ZnO doped with 2.9% by weight of Mn and 3.2% by weight of Mg)

P2: Sicopal Orange FK 4055 (ZnO doped with 7.0% by weight of Mn and 1.6% by weight of Mg)

*): Sicomet White E 171

TABLE

| | A | B | C | D |
|---|---|---|---|---|
| Lipstick base (% by weight) | 85.0 | 94.5 | 85.0 | 94.5 |
| Color pigment (% by weight) | 15.0 of P1 | 5.0 of P1 0.5 of *) | 15.0 of P2 | 5.0 of P1 0.5 of *) |

EXAMPLE 2

Preparation of a make-up

A make-up was prepared according to the following recipe:

45 2.0% of glycerol monostearate
2.0% of cetyl alcohol
2.0% of Cremophor A6
2.0% of Cremophor A 25
5.5% of Miglyol 812
5.0% of paraffin oil
4.5% 1,2-propylene glycol
qs of preservative
61.0% of distilled water
0.5% of Sicovil Black 85
15.0% of Sicopal Yellow FK 4165 (or Sicopal Orange FK 4055)

EXAMPLE 3

Preparation of an eye-shadow

An eye-shadow was prepared according to the following recipe:

20.0% of talc
10.1% of potato starch
5.2% of magnesium stearate
16.1% of binder*
48.6% of Sicopal Yellow FK 4165 (or Sicopal Orange FK 4055)

* Binder:

2.0% of glycerol monostearate
2.0% of cetyl alcohol
2.0% of Cremophor A 6
2.0% of Miglyol 812
5.0% of 1,2-propylene glycol
qs of preservative
75.0% of water

We claim:

1. A cosmetic composition comprising metal ion-doped colored zinc oxides said oxides further comprising iron, manganese, magnesium, calcium, or a combination thereof in the form of divalent metal oxides.

2. A process for coloring decorative cosmetics comprising adding therein the cosmetic composition of claim 1.

3. The process of claim 2 wherein the decorative cosmetics comprise eye cosmetics.

4. The process of claim 2 wherein the decorative cosmetics comprise make-up.

5. The process of claim 2 wherein the decorative cosmetics comprise lipsticks.

6. The process of claim 2 wherein the decorative cosmetics comprise nail varnishes.

* * * * *

UNITED STATES PATENT AND TRADEMARK OFFICE

CERTIFICATE OF CORRECTION

PATENT NO.: 5,800,824

DATED: September 1, 1998

INVENTOR(S): PFROMMER et al.

It is certified that error appears in the above-identified patent and that said Letters Patent is hereby corrected as shown below:

On the cover page, insert the following foreign priority information:

--[30] Foreign Application Priority Data
Oct. 9, 1995 [DE] Germany .............. 195 37 480.0--.

Signed and Sealed this

Twenty-second Day of December, 1998

Attest:

BRUCE LEHMAN

*Attesting Officer* *Commissioner of Patents and Trademarks*